United States Patent [19]

Alexanderson et al.

[11] 4,091,042
[45] May 23, 1978

[54] CONTINUOUS ADIABATIC PROCESS FOR THE MONONITRATION OF BENZENE

[75] Inventors: Verner Alexanderson, Plainfield; James Bryan Trecek, Bridgewater; Cornelius Marsden Vanderwaart, Basking Ridge, all of N.J.

[73] Assignee: American Cyanamid Company, Stamford, Conn.

[21] Appl. No.: 826,208

[22] Filed: Aug. 19, 1977

[51] Int. Cl.² .................... C07C 79/10; C07C 79/12
[52] U.S. Cl. ................................ 260/645; 203/12; 203/88
[58] Field of Search ................. 260/645; 203/12, 88

[56] References Cited

U.S. PATENT DOCUMENTS

| | | | |
|---|---|---|---|
| 3,087,971 | 4/1963 | Samuelsen | 260/645 |
| 3,243,466 | 3/1966 | Brogden et al. | 260/645 |
| 3,928,475 | 12/1975 | Dassel | 260/645 |

Primary Examiner—Leland A. Sebastian
Attorney, Agent, or Firm—William J. van Loo

[57] ABSTRACT

Benzene is admixed and reacted continuously with a mixed acid containing 3–7.5% nitric acid, 58.5–66.5% sulfuric acid, and 28–37% water under pressure sufficient to maintain benzene in liquid state until complete conversion of nitric acid is achieved to provide mononitrobenzene containing less than 500 ppm dinitrobenzene.

3 Claims, No Drawings

CONTINUOUS ADIABATIC PROCESS FOR THE MONONITRATION OF BENZENE

The present invention relates to an improved continuous process for the manufacture of mononitrobenzene. More particularly, it relates to an improved continuous adiabatic process for the mononitration of benzene to mononitrobenzene.

The nitration of nitratable aromatic compounds is old and well-known. The nitration of benzene in particular is widely practiced commercially to produce mononitrobenzene for the manufacture of aniline.

Current commercial technology for the manufacture of nitrobenzene consists basically of either a batchwise or continuous addition of a mixture of sulfuric and nitric acid, commonly called mixed acid, to benzene. The nitration reaction is ordinarily conducted at a temperature in the range of about 60° C to 70° C or lower, and the processes involve removal of heat of reaction by cooling. Mixed acids ordinarily contain a high nitric acid content, i.e., about 20–30%, and as a result the volume of the mixed acid is low; the ratio of mixed acid to benzene ranging from about 2.9 to 3.6 to 1. The spent acid, i.e., the mixed acid following reaction, which is essentially completely depleted of nitric acid, is then reconcentrated to 93–95% sulfuric acid or fortified with sulfur trioxide or oleum to 100–105% for recycle.

The inherent disadvantages of the currently used processes, especially the extensive cooling required to remove heat of reaction, was recognized many years ago by Castner (U.S. Pat. No. 2,256,999) who disclosed an adiabatic nitration process in which the total heat of mixing and heat of reaction was retained and utilized in the reaction to increase the rate and also to raise the temperature of the spent acid to a peak of about 100° C, thereby permitting more efficient concentration of the spent acid by conventional means, such as flash evaporation. The Castner adiabatic process, insofar as we are aware, has not met with commercial success, as evidenced by the continued widespread use of the aforementioned current commercial technology.

The disadvantages inherent in the Castner process were overcome to a large extent by Alexanderson et al., U.S. Pat. No. 4,021,498, wherein a process is described which utilizes an adiabatic nitration reaction characterized by the use of a mixed acid containing not less than 25% water and a reaction temperature which does not exceed about 145° C to produce nitrobenzene containing less than about 500 parts per million of dinitrobenzene.

The process described by Alexanderson et al. was based on the discovery that when the amount of water in the mixed acid is controlled and, as a result, the concentration of the spent acid is kept below about 72% sulfuric acid, excessive dinitration is avoided. However, the process was limited to a maximum temperature of reaction of about 80° C at atmospheric pressure.

We have now discovered an improved continuous adiabatic nitration process whereby, under certain restricted conditions, defined hereinbelow, it is possible to produce mononitrobenzene, substantially free of dinitrobenzene, at much higher temperatures, thereby markedly increasing both the rate of reaction and the throughput. The process provides substantial advantages over existing technology in that by its use productivity is significantly increased without any significant accompanying disadvantages.

In accordance with the present invention a reaction stream of a mixed acid containing from about 3 to 7.5 percent nitric acid, from about 58.5 to 66.5 percent sulfuric acid and from about 28 to 37 percent water, and a reaction stream of up to about a 10 percent stoichiometric excess of benzene, are continuously admixed and reacted under the influence of vigorous agitation at a temperature in the range of about 80° C to 120° C at superatmospheric pressure, in a manner such that the reaction temperature does not exceed about 145° C, to produce a high yield, i.e., essentially complete conversion of nitric acid, of mononitrobenzene containing less than about 500 parts per million of dinitrobenzene.

As used herein, the term superatmospheric pressure means a pressure sufficient to keep the benzene in the reaction mixture in the liquid state at the reaction temperature used.

Vigorous agitation, as used herein, means sufficient agitation to uniformly disperse the liquid benzene throughout the reaction mixture at all times during the reaction to enhance the reaction thereof with the nitric acid.

The spent acid concentration following the nitration must fall within the range of about 62 to 68 percent sulfuric acid. It will be recognized that not every combination of nitric acid, sulfuric acid and water set forth above will provide a spent acid falling within the range 62 to 68% sulfuric acid. For instance, a mixed acid consisting of 3% nitric acid and 58.5% sulfuric acid is too dilute in sulfuric acid and a mixed acid consisting of 7.5% nitric acid and 66.5% sulfuric acid is too concentrated in sulfuric acid. Such compositions will result in too low and too high a spent acid concentration, respectively.

When the nitric acid concentration of the mixed acid is appreciably less than about 3 percent, the volume of the mixed acid relative to the benzene becomes excessive and the process becomes uneconomical; when the nitric acid concentration appreciably exceeds about 7.5 percent, the heat generated by the reaction in the specified temperature range will cause the temperature to rise too high, i.e., in excess of 145° C, and increased dinitration will result.

When the water concentration of the mixed acid is appreciably less than about 28 percent, the reaction will produce excessive dinitration, and if appreciably greater than about 37 percent the rate of the reaction slows appreciably, leading to lower conversion of the nitric acid to nitrobenzene.

When the spent acid concentration is appreciably less than about 62 percent sulfuric acid, the rate of reaction slows significantly; and, if appreciably higher than about 68 percent sulfuric acid, increased dinitration will result.

Although there is nothing inherently deleterious in operating the process of the invention under uneconomical conditions, i.e., lower than 3 percent nitric acid, greater than 37 percent water or less than 62 percent spent sulfuric acid, it will be recognized by those skilled in the art that such conditions will result in lower conversion and slow rate of reaction, and will result also in appreciable nitric acid concentration in the spent acid, which must either be recovered or lost. Thus, it is preferred to operate the process under the aforementioned conditions in order to achieve at least about 98 percent conversion of the nitric acid, and still more preferably, at least about 99 percent conversion of nitric acid. On the other hand, operation of the process using greater than about 7.5 percent nitric acid, less than about 28 percent water or greater than about 68 percent spent sulfuric acid will result in the formation of undesirably high concentrations, i.e., in excess of about 500 parts per million, of dinitrobenzene in the product.

It will be recognized that not every combination of mixed acid concentrations within the ranges stated may be used at every temperature within the 80° C to 120° C range stated. The maximum reaction temperature should not exceed about 145° C in order to avoid the formation of dinitration by-products. Thus, mixed acids high in nitric acid will in general be used at the lower temperatures and mixed acids low in nitric acid at the higher temperatures.

It is important in the operation of the present process to control the amount of water in the mixed acid and, accordingly, in the spent sulfuric acid, within the ranges set forth. In so doing, it is possible to nitrate benzene to mononitrobenzene at appreciably higher temperatures than heretofore possible in an adiabatic process without the concomitant formation of dinitrobenzene. The present process thereby has the advantage of greatly increased rate of reaction and greatly increased throughput and provides very high yields, based on nitric acid conversion, of high quality mononitrobenzene.

The process of the present invention is not limited to any particular mechanical or equipment means or assemblage thereof. However, for illustrative purposes the process is conducted continuously, preferably using a series of four continuous overflow, stirred tank nitration reactors. Thus, a benzene feed stream at room temperature and a mixed acid feed stream, heated to a temperature in the range 80° C to 120° C, are fed into the bottom of the first of the reactors to form a nitration reaction mixture which overflows and is fed into the bottom of the second reactor and so forth. The mixed acid is formed continuously in a mixing tee by blending 68.5 percent sulfuric acid and 60 percent nitric acid. The contents of the reactors are under a positive pressure sufficient to keep the benzene in the liquid state. The residence time in each reactor will depend on the volume of the reaction mixture and on the feed rate and on the reaction temperature.

The reaction mixture overflowing from the fourth nitration reactor is continuously fed to a continuous phase separator where the spent acid is separated from the organic phase. The spent acid is then reconcentrated using a vacuum flash evaporator, utilizing the heat generated in the reaction. The concentration of the spent acid using flash evaporators or other means is old and well-known.

The organic phase is continuously fed into a four-stage, counter-current, washer-extractor where acidic components, such as entrained sulfuric acid, dinitrophenol and picric acid, are removed by contact with a sodium carbonate solution. The washed organic phase is then steam stripped to recover excess benzene. The benzene and reconcentrated sulfuric acid are recycled. The product remaining contains less than about 500 parts per million of dinitrobenzene.

EXAMPLE 1

Benzene (10% stoichiometric excess) and mixed acid containing 5.2% nitric acid, 62.5% sulfuric acid and 32.3% water, are continuously mixed and fed into the bottom of the first of four continuous overflow, stirred-tank, nitration reactors. The benzene is fed at room temperature and the mixed acid is heated to 90° C. Pressure on the reactor is 65 psig. Following a residence time of 2.8 minutes in the first reactor the reaction temperature is 132° C ($\Delta T = 42°$ C) and conversion of nitric acid to nitrobenzene is 91%. The reaction mixture flows into the bottom of the second reactor and, following a residence time of 2.8 minutes, the temperature is 135° C ($\Delta T = 45°$ C) and conversion is 98%. The reaction is continued in this manner so that the reaction mixture, following overflow from the third and fourth reactors after 2.8 minutes residence time in each reactor, has a temperature of 135.5° C and 136° C, respectively, and a degree of conversion of 99% and 99.5%, respectively. Total residence time is 11.2 minutes.

The flow from the fourth reactor is fed into a continuous separator, where the spent acid, which is 65% sulfuric acid, is separated from the organic phase.

The spent acid is then reconcentrated to 68% sulfuric acid in a vacuum flash evaporator operating at 90° C and 60 mm Hg. The acid is recycled.

The organic phase is continuously fed to a four-stage counter-current, washer-extracter, where entrained sulfuric acid, dinitrophenol (0.1%) and picric acid (0.1%) are removed by contact with a solution of sodium carbonate. The washed organic phase is then steam stripped to remove unreacted, excess benzene. The product nitrobenzene contains <100 parts per million of dinitrobenzene.

EXAMPLE 2

Following the procedure of Example 1, benzene and a mixed acid comprised of 3% nitric acid, 66.5% sulfuric acid and 30.5% water, heated to a temperature of 120° C, are reacted under a pressure of 65 psig. The residence time in each reactor is 0.3 minute and the spent acid concentration is 68%. The degree of conversion and temperature in each reactor are:

| Reactor No. | % Conversion | Temperature ° C |
|---|---|---|
| 1 | 90 | 142 |
| 2 | 96 | 144 |
| 3 | 98 | 144.5 |
| 4 | 99 | 145 |

The product contains less than 100 parts per million of dinitrobenzene.

EXAMPLE 3

Following the procedure of Example 1, benzene and a mixed acid comprised of 7.4% nitric acid, 58.6% sulfuric acid and 34% water, heated to a temperature of 80° C, are reacted under a pressure of 65 psig. The residence time in each reactor is 5 minutes. The spent acid is 62% sulfuric acid. The degree of conversion and temperature in each reactor are as follows:

| Reactor No. | % Conversion | Temperature ° C |
|---|---|---|
| 1 | 82 | 133 |
| 2 | 94 | 141 |
| 3 | 98 | 144 |
| 4 | 99 | 145 |

The product contains less than 100 parts per million of dinitrobenzene.

EXAMPLES 4 - 9

In a manner similar to Example 1, a reactant stream at 80° C containing 67.02% sulfuric acid, 5.95% nitric acid and 27.03% water, and a reactant stream of benzene at room temperature, were continuously mixed and reacted under rigorous agitation. The mixed acid feed rate was 116 ml/min. (ratio benzene : nitric acid = 1.05). The residence time was 2 minutes. In successive experiments the mixed acid was diluted by the addition of water, as shown in the accompanying table, and the mixed acid feed rate was adjusted to maintain the same benzene : nitric acid ratio; residence time remained the same.

|  | EXAMPLE NO. | | | | | |
|---|---|---|---|---|---|---|
|  | 4 | 5 | 6 | 7 | 8 | 9 |
| Mixed Acid, Grams | | | | | | |
| $H_2SO_4$ | 125.94 | — | — | — | — | — |
| $HNO_3$ | 11.18 | — | — | — | — | — |
| $H_2O$ | 50.79 | — | — | — | — | — |
| Water Added, Grams | 0 | 2.6 | 5.3 | 8.06 | 13.86 | 20.03 |
| Total Mixed Acid, Grams | 187.91 | 190.51 | 193.21 | 195.97 | 201.77 | 207.94 |
| % $H_2SO_4$ | 67.02 | 66.11 | 65.18 | 64.26 | 62.42 | 60.57 |
| % $HNO_3$ | 5.95 | 5.87 | 5.79 | 5.70 | 5.54 | 5.38 |
| % $H_2O$ | 27.03 | 28.02 | 29.03 | 30.03 | 32.04 | 34.06 |
| Spent Acid, % $H_2SO_4$ | 70.00 | 69.00 | 67.99 | 67.00 | 64.99 | 62.99 |
| Final Temperature, ° C | 133 | 134 | 134 | 132 | 127 | 123 |
| Product, % | | | | | | |
| Benzene | 0.28 | 0.65 | 0.43 | 4.95 | 4.00 | 10.4 |
| MNB* | 98.71 | 98.8 | 99.12 | 95.6 | 96.94 | 89.5 |
| DNB** | 0.12 | 0.06 | 0.029 | 0.012 | ND | ND |
| DNP*** | 0.18 | 0.18 | 0.18 | 0.15 | 0.13 | 0.10 |

*mononitrobenzene
**dinitrobenzene
***50/50 mixture dinitrophenol and picric acid
ND = none detected The data show that Experiments No. 4 and 5, which have spent acid concentration greater than 68%, produce 1200 and 600 parts per million of dinitrobenzene; that Experiment No. 6 has very high conversion and low DNB (290 ppm); that Experiments No. 7–9 have successively lower spent acid concentration and lower conversion, indicating the need for additional reaction time or higher reaction temperature. The examples illustrate the importance of the role of water in the process of the invention.

We claim:

1. In an adiabatic process for the mononitration of benzene with nitric acid to produce mononitrobenzene, whereby a reactant stream of benzene and a reactant stream of a mixed acid comprising nitric acid, sulfuric acid and water are contacted at an elevated temperature to produce a nitration reaction mixture; whereby the heat of mixing and heat of reaction produced thereby is absorbed by said reaction mixture and utilized therein in the nitration reaction; whereby the product of the reaction, consisting of an organic phase containing said mononitrobenzene and an aqueous phase consisting essentially of hot aqueous sulfuric acid are separated; and whereby said organic phase is washed free of acidic by-products to yield said mononitrobenzene, the improvement which comprises: contacting a reactant stream of a stoichiometric excess of benzene and a reactant stream of a mixed acid, comprising from about 3 to 7.5 percent by weight of nitric acid, from about 58.5 to 66.5 percent by weight of sulfuric acid and from about 28 to 37 percent by weight of water, to form a nitration reaction mixture at a temperature in the range of from about 80° C to 120° C under superatmospheric pressure sufficient to maintain said benzene in said reaction mixture in the liquid state; subjecting said reaction mixture to vigorous agitation for a period of time sufficient to convert substantially all of said nitric acid to mononitrobenzene; separating said reaction product composition, at a temperature not in excess of about 145° C, into an organic phase and an aqueous sulfuric acid phase, said aqueous sulfuric acid phase containing essentially no nitric acid and comprising from about 62 to 68 percent by weight of sulfuric acid; and recovering said mononitrobenzene from said organic phase, said mononitrobenzene being characterized as containing less than about 500 parts per million of dinitrobenzene.

2. The process according to claim 1 wherein at least about 98 percent of said nitric acid is converted to mononitrobenzene.

3. The process according to claim 1 wherein said aqueous sulfuric acid phase is reconcentrated to its original concentration by vacuum flash evaporation utilizing the heat generated in said reaction.